(12) United States Patent
Gagnon

(10) Patent No.: US 10,413,267 B2
(45) Date of Patent: Sep. 17, 2019

(54) METHOD AND APPARATUS FOR PERFORMING CO-PLANAR AND SIMULTANEOUS SPECTRAL CT AND PET IMAGING

(71) Applicant: Daniel Gagnon, Twinsburg, OH (US)

(72) Inventor: Daniel Gagnon, Twinsburg, OH (US)

( * ) Notice: Subject to any disclaimer, the term of this patent is extended or adjusted under 35 U.S.C. 154(b) by 0 days.

(21) Appl. No.: 15/584,726

(22) Filed: May 2, 2017

(65) Prior Publication Data
US 2017/0311919 A1 Nov. 2, 2017

Related U.S. Application Data

(60) Provisional application No. 62/330,654, filed on May 2, 2016.

(51) Int. Cl.
| | | |
|---|---|---|
| A61B 6/00 | (2006.01) | |
| A61B 6/02 | (2006.01) | |
| A61B 6/03 | (2006.01) | |
| A61B 6/10 | (2006.01) | |
| A61B 5/055 | (2006.01) | |
| G01T 1/161 | (2006.01) | |
| G01N 23/046 | (2018.01) | |

(52) U.S. Cl.
CPC ............ *A61B 6/5235* (2013.01); *A61B 6/032* (2013.01); *A61B 6/037* (2013.01); *A61B 6/107* (2013.01); *A61B 6/4241* (2013.01); *A61B 6/4258* (2013.01); *A61B 6/4417* (2013.01); *A61B 6/482* (2013.01); *A61B 6/50* (2013.01); *A61B 6/5247* (2013.01); *G01N 23/046* (2013.01); *G01T 1/161* (2013.01); *A61B 5/0555* (2013.01); *A61B 6/027* (2013.01)

(58) Field of Classification Search
CPC ....... A61B 6/5235; A61B 6/032; A61B 6/037; A61B 6/107; A61B 6/4241; A61B 6/4258; A61B 6/4417; A61B 6/482; A61B 6/50; A61B 6/5247; A61B 6/027; A61B 5/0555; G01N 23/046; G01T 1/161
USPC ............. 250/363.02, 363.03, 363.04, 363.05
See application file for complete search history.

(56) References Cited

U.S. PATENT DOCUMENTS

| | | | | |
|---|---|---|---|---|
| 5,705,819 A * | 1/1998 | Takahashi | ............... | A61B 6/037 250/363.02 |
| 6,700,949 B2 * | 3/2004 | Susami | ................ | A61B 6/4417 250/363.03 |
| 7,447,345 B2 * | 11/2008 | Shanmugam | .......... | A61B 6/032 250/363.03 |
| 8,260,013 B2 * | 9/2012 | Pekar | ..................... | A61B 6/032 250/363.04 |
| 8,594,404 B2 * | 11/2013 | Yamaya | ................ | G01T 1/1611 250/363.02 |

(Continued)

*Primary Examiner* — David P Porta
*Assistant Examiner* — Blake C Riddick
(74) *Attorney, Agent, or Firm* — Wegman, Hessler

(57) ABSTRACT

A PET/CT imaging system is provided. The imaging system includes a PET detection system having a plurality of detector rings and an axial gap between at least two adjacent detector rings within the plurality of detector rings. The imaging system includes a CT system having an x-ray generator and a CT detection system positioned within the axial gap between the at least two detector rings. The system is configured to collect PET data and CT data on the same volume of interest substantially simultaneously.

22 Claims, 11 Drawing Sheets

(56) References Cited

U.S. PATENT DOCUMENTS

| | | | | |
|---|---|---|---|---|
| 8,630,696 B2* | 1/2014 | Kim | A61B 6/032 | 250/363.03 |
| 2002/0090050 A1* | 7/2002 | Nutt | A61B 6/032 | 378/19 |
| 2005/0089141 A1* | 4/2005 | Brown | A61N 5/10 | 378/65 |
| 2007/0080295 A1* | 4/2007 | Hamill | G01T 1/2985 | 250/363.03 |
| 2008/0103391 A1* | 5/2008 | Dos Santos Varela | G01T 1/1615 | 600/436 |
| 2009/0154647 A1* | 6/2009 | Matsuzawa | A61B 6/032 | 378/98 |
| 2009/0304141 A1* | 12/2009 | Nakazawa | A61B 6/032 | 378/5 |
| 2010/0040197 A1* | 2/2010 | Maniawski | A61B 6/032 | 378/65 |
| 2010/0102239 A1* | 4/2010 | Hahn | G06T 5/50 | 250/363.05 |
| 2010/0128956 A1* | 5/2010 | Yamaya | G01T 1/1611 | 382/132 |
| 2010/0166137 A1* | 7/2010 | Sawanaga | A61B 6/032 | 378/4 |
| 2012/0046544 A1* | 2/2012 | Inoue | A61B 6/037 | 600/425 |
| 2012/0114212 A1* | 5/2012 | King | G06T 11/006 | 382/131 |
| 2013/0322717 A1* | 12/2013 | Bar-Shalev | G06T 7/0044 | 382/131 |
| 2014/0249408 A1* | 9/2014 | Collins | A61B 6/032 | 600/427 |
| 2015/0018673 A1* | 1/2015 | Rose | A61B 5/0035 | 600/427 |
| 2015/0275080 A1* | 10/2015 | Ronda | C04B 35/01 | 250/362 |
| 2015/0323685 A1* | 11/2015 | Nelson | G01T 1/1611 | 250/370.08 |
| 2016/0183893 A1* | 6/2016 | Zhang | A61B 6/0407 | 250/363.05 |
| 2016/0209514 A1* | 7/2016 | Moskal | G01T 1/2985 | |

* cited by examiner

METHOD AND APPARATUS FOR PERFORMING CO-PLANAR AND SIMULTANEOUS SPECTRAL CT AND PET IMAGING

CROSS-REFERENCE TO RELATED APPLICATIONS

This application claims benefit of U.S. Provisional Patent Application Ser. No. 62/330,654, filed May 2, 2016, and entitled "METHOD AND APPARATUS FOR PERFORMING CO-PLANAR AND SIMULTANEOUS SPECTRAL CT AND PET IMAGING", which is herein incorporated by reference in its entirety.

FIELD OF THE INVENTION

Aspects of the disclosed technology relate to hybrid imaging, and, more particularly, to a combined PET/CT imaging system and method.

BACKGROUND

Hybrid Imaging—where multiple imaging modalities are performed on the same subject in the same imaging session—was brought to medicine over a decade ago. For example, the introduction of a combined positron emission tomography (PET) and computed tomography (CT) scanner in the early 2000s has pioneered this field that now includes many more elements, like PET/MR, SPECT/CT, CT/XR, MR/UL and more. The benefits of hybrid imaging are multi-fold. First, two (or more) types of contemporary information on the patient can be clinically relevant. If the information are complementary, it can add to the quality of the convergence of the diagnostic. If the information are correlated, it adds to the certainty of the analysis. Second, there can be a benefit for the patient who has more information extracted from one single test. Third, it can streamline the administrative tasks (e.g., scheduling) and interpretation (e.g., the same physician reading the PET and the CT) where the exam is being performed.

BRIEF SUMMARY

Aspects of the disclosed technology relate to a system and a method to have computed tomography (CT) and the positron emission tomography (PET) sub-systems operate on substantially the same volume at the same time and to allow the CT sub-system to optimally perform in a spectral acquisition mode or multi-energy mode.

One aspect of the disclosed technology relates to a PET/CT imaging system that includes a PET detection system comprising a plurality of detector rings, wherein at least two adjacent detector rings within the plurality of detector rings are positioned with an axial space between the at least two adjacent detector rings; a CT system comprising an x-ray generator and a CT detection system, wherein the x-ray generator is positioned and configured to generate an x-ray beam within the axial space between the at least two adjacent detector rings for detection by the CT detection system; and a processor operatively coupled to the PET detection system and the CT detection system, wherein in response to simultaneously acquired radiation by the PET detection system and the CT detection system, the processor is configured to process signals received from the PET detection system and the CT detection system independently and/or jointly.

Another aspect of the disclosed technology relates to an imaging method for imaging a given region of interest (ROI), the imaging method being carried out using a PET/CT imaging system. The PET/CT imaging system includes a PET detection system comprising a plurality of detector rings, wherein at least two adjacent detector rings within the plurality of detector rings are positioned with an axial space between the at least two adjacent detector rings; and a CT system comprising an x-ray generator and a CT detection system, wherein the x-ray generator is positioned and configured to generate an x-ray beam within the axial space between the at least two adjacent detector rings for detection by the CT detection system. The imaging method includes simultaneously collecting PET imaging data using the PET detection system and CT imaging data using the CT system for a given imaging time.

According to one feature, the PET detection system has a standard PET imaging time for the given ROI and the CT system has a standard CT imaging time for the given ROI, and wherein the imaging time for the simultaneous collecting of PET imaging data and CT imaging data is approximately equal to the standard PET imaging time.

According to one feature, the PET detection system has a standard PET imaging time for the given ROI and the CT system has a standard CT imaging time for the given ROI, and wherein the imaging time for the simultaneous collecting of PET imaging data and CT imaging data is approximately equal to at least 10 times the standard CT imaging time.

According to one feature, the PET detection system has a standard PET imaging time for the given ROI and the CT system has a standard CT imaging time for the given ROI, and wherein the imaging time for the simultaneous collecting of PET imaging data and CT imaging data is approximately equal to from about least 10 times the standard CT imaging time to about 100 times the standard CT imaging time.

According to one feature, the imaging method includes processing signals representative of the simultaneously collected PET imaging data and CT imaging data independently and/or jointly.

According to one feature, the imaging time for collecting the CT imaging data is no less than about 10 seconds.

According to one feature, the imaging time for collecting the CT imaging data is between about 10 second and about 100 seconds.

According to one feature, the CT imaging data is collected in an axial step-and-shoot mode.

According to one feature, the PET/CT imaging system includes a radiation shield disposed at least partially over a circumference of the detector rings of the PET detection system, wherein the radiation shield is configured to rotate in synchronization with the x-ray generator and the CT detection system.

According to one feature, the radiation shield is disposed over the entire axial extent of the detector rings of the PET detection system.

According to one feature, the radiation shield is disposed over a portion of the axial extent of the detector rings of the PET detection system.

According to one feature, the radiation shield is comprised of a single homogeneous material.

According to one feature, the radiation shield is comprised of one or more layers of material.

Another aspect of the disclosed technology relates to a PET/CT imaging system that includes a PET detection arrangement comprising at least one detector ring, wherein the at least one detector ring of the PET detection arrangement has an axial dimension; a CT system comprising an x-ray generator and a CT detection arrangement, the x-ray generator being configured to generate an x-ray beam having an axial dimension for detection by the CT detection arrangement; wherein the PET/CT imaging system is configured such that an edge of the x-ray beam generated by the x-ray generator is spaced no more than about 5 centimeters from an edge of the at least one ring on the PET detection arrangement along the axial dimension; and a processor operatively coupled to the PET detection arrangement and the CT detection arrangement, wherein in response to simultaneously acquired radiation by the PET detection arrangement and the CT detection arrangement, the processor is configured to process signals received from the PET detection arrangement and the CT detection arrangement independently and/or jointly.

These and further features of the disclosed technology will be apparent with reference to the following description and attached drawings. In the description and drawings, particular embodiments or aspects of the disclosed technology have been disclosed in detail as being indicative of some of the ways in which the principles of the disclosed technology may be employed, but it is understood that the disclosed technology is not limited correspondingly in scope. Rather, the disclosed technology includes all changes, modifications and equivalents coming within the spirit and terms of the claims appended thereto.

Features that are described and/or illustrated with respect to one embodiment may be used in the same way or in a similar way in one or more other embodiments and/or in combination with or instead of the features of the other embodiments.

It should be emphasized that the term "comprises/comprising" when used in this specification is taken to specify the presence of stated features, steps or components, but does not preclude the presence or addition of one or more other features, steps, components or groups thereof.

DRAWINGS

These and other features of the disclosed technology, and its advantages, are illustrated specifically in embodiments now to be described, by way of example, with reference to the accompanying diagrammatic drawings.

FIG. 1A and FIG. 1B are diagrammatic illustrations of a PET acquisition illustrating principles related to the disclosed technology;

FIG. 2 A is a diagrammatic illustration of a portion of a PET acquisition illustrating principles related to the disclosed technology;

Figure 1A:
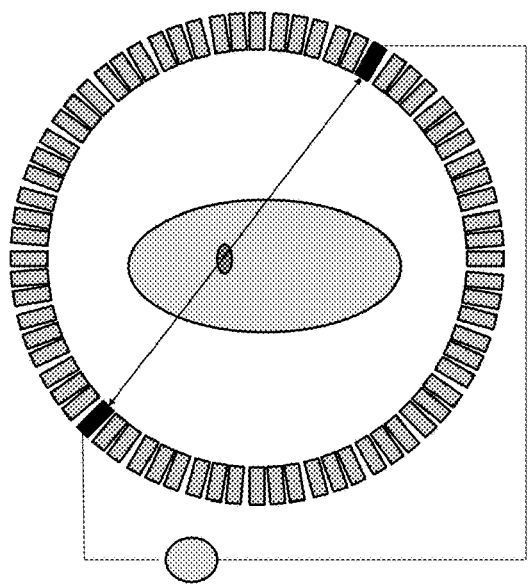

It should be noted that all the drawings are diagrammatic and not drawn to scale. Relative dimensions and proportions of parts of these figures have been shown exaggerated or reduced in size for the sake of clarity and convenience in the drawings. The same reference numbers are generally used to refer to corresponding or similar features in the different embodiments. Accordingly, the drawing(s) and description are to be regarded as illustrative in nature and not as restrictive.

DETAILED DESCRIPTION AND DRAWINGS

The present disclosure recognizes that the desire to combine existing imaging modalities has historically forced a series of compromises to make the systems co-exist with each other. One example of this is in the field of PET/MR (magnetic resonance), where the first attempt forced suboptimal PET detection systems to be used. The PET detection system made use of slower solid-state detectors for the detection system to function in an intense magnetic field (although many of these problems have been eliminated with the recent introduction of Silicon Photomultipliers (SiPM), having much better performances that the earlier avalanche photo-diodes). Even for PET/CT, where technically both systems are operating in the same type of conditions on similar signals (x-ray and gamma-ray), the CT technology inside a PET/CT has traditionally lagged the stand-alone CT by many years, and, more significantly, PET/CT has never resolved the co-planarity of the two images. In conventional systems, PET/CT data acquisitions have been sequential in time, and separated by a distance varying from a few tens of centimeters, to almost one meter.

Figure 1B:
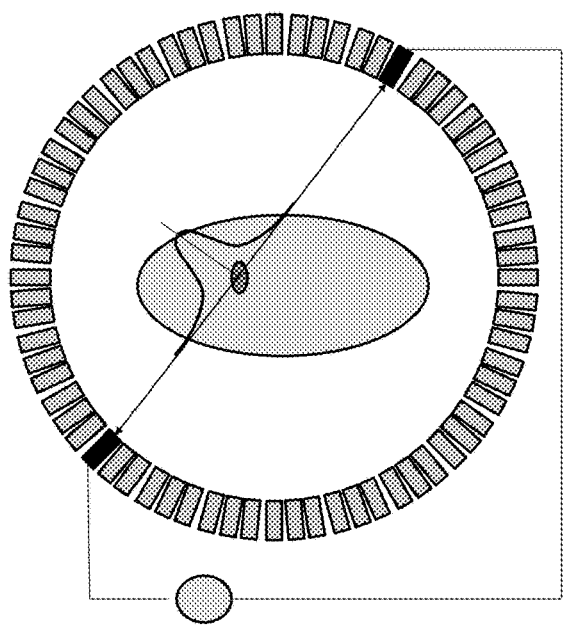

With reference to FIG. 1A and FIG. 1B, it will be appreciated that optimal PET imaging is performed by forming different Lines-of-Response (LOR) by identifying detections that are in coincidence from different locations on a detector ring (e.g., the blocks on the diagram connected by a line). For simplicity, other conditions like scattered and random events are not described in this diagrammatic illustration. For typical imaging conditions, it will be appreciated that roughly 25% of the events would be put in coincidence but should not (so called "randoms"), and another 25% of the rays will undergo one or more interactions inside the patient before reaching the detector (scatter), but the essence of the following argument remains.

Furthermore, if the timing accuracy of the circuitry is sufficient, the analysis of the different time-of-arrival can establish not only a line on which the event has occurred, but where on the line the event is most likely to originate from.

It will be appreciated that the Gaussian shape (line on the LOR) shown in FIG. 1B is directly related to the timing accuracy of the system. Theoretically, with enough accuracy, each detection could be assigned to a unique location in the object (without further needs of processing).

Since the timing accuracy in modern commercial systems is between 500 and 300 picoseconds, or a width of the Gaussian of few tens of centimeters, exact positioning of the event currently is not possible, and a tomographic reconstruction process has to be implemented. With "enough" events, an image can be reconstructed. In this context, "enough counts" can be an evasive concept that will depend on many factors, including the size the object, the target-to-background ratio, the size of the object of interest (e.g., tumor), the type of imaging task (e.g., simple detection (absence/presence), or characterization (exact shape, size, intensity)).

It is known, however, from practice that for a typical test (e.g., $^{18}$FDG imaging) for typical patient (e.g., 80 kilograms), for a typical (maximum) injected dose (e.g., about 8 to about 12 millicurie), a few hundred million events will be required, and commercially available scanners should able to gather that amount of counts between 5 and 10 minutes of continuous detection over a 100 centimeter long section of the patient. This "whole-body" protocol currently represent the majority of all PET studies performed. Other studies are concentrating over a smaller areas, heart or brain for instance, but the 5 to 10 minutes of required acquisition time remains.

The above description of an exemplary PET study is mostly describing what is happening in the transaxial plane (plane perpendicular to the long axis of the patient or the imaging ring). It will be appreciated that the PET detection ring extends in the axial direction and an entire volume is being collected at the same time, not only a plane.

Figure 2A:
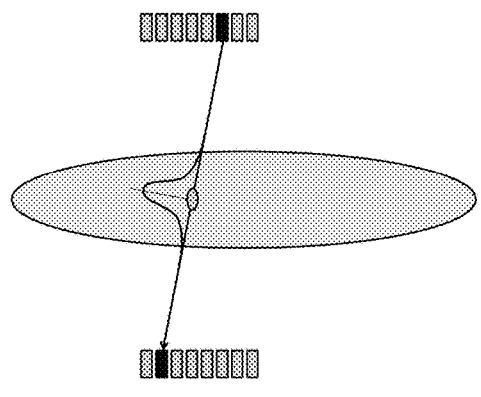
FIG. 2B is a diagrammatic illustration of a portion of a pet acquisition in which the PET detector includes an axial gap in accordance with aspects of the disclosed technology.
Figure 2B:
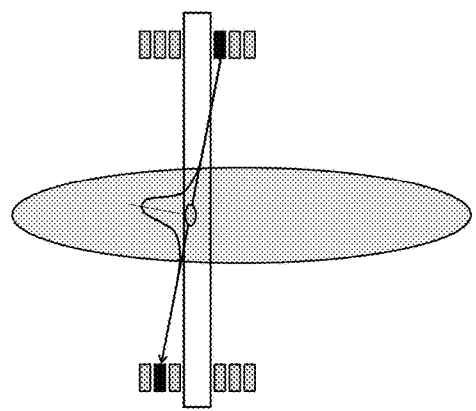

With reference to FIG. 2A and FIG. 2B, it will be appreciated that the same principles will apply in the axial plane, and LORs can be formed within a transaxial plane (e.g., exactly opposite detectors on the same ring) or cross-planes like in the example given below. Similarly to the transaxial plane, the addition of the Time-of-Flight (TOF) information will provide information as to which plane the event originated.

There is, however, an additional benefit of the TOF information in the transaxial direction. It will be appreciated that the additional oblique (between planes) information could allow for or compensate for a gap in the ring distribution. Meaning that the (part of the) object in the area defined by the gap (see, FIG. 2B, for example), could be imaged with similar quality, provided that the TOF information (or timing resolution) is sufficient.

As is described more fully below, the PET/CT imaging system in accordance with the disclosed technology, makes use of this gap to insert a CT system.

It will be appreciated that the principle of CT imaging is the collection of how an object (e.g., a patient) affects the x-ray flux from a generator (also referred to simply as an x-ray source). The computation, ray-by-ray, of the ratio of the intensity detected with the object present to what it should have been without it, will allow for the definition of the attenuation map via the tomographic reconstruction principle.

Figure 3:
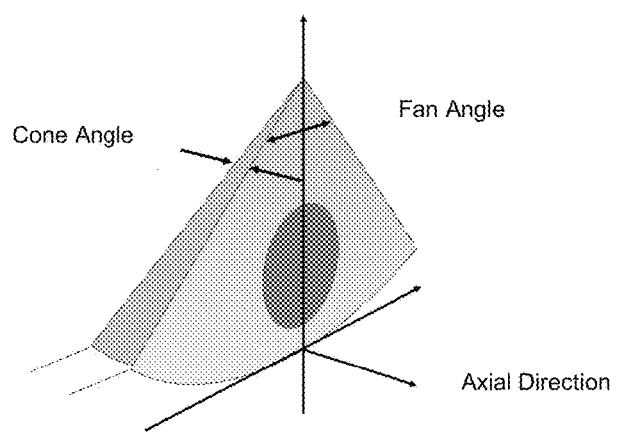
FIG. 3 is a diagrammatic illustration of an exemplary x-ray beam configuration used in connection with aspects of the disclosed technology.

Typically, a CT system will include an x-ray tube generating a precise fan (in the transaxial plane) and a cone (in the axial plane) (see FIG. 3, for example), a detector array, typically on an arc, with a fixed geometry with respect to the x-ray tube. A mechanical arrangement allows (sometimes referred to as a gantry or a rotating gantry) the combination of x-ray tube and detector to rotate around the object keeping the same geometrical relationship between each other. It will be appreciated that many other systems and other correction apparatuses exist not shown in this simple configuration.

The overall attributes of CT imaging have evolved over the past decades to become very impressive with spatial and temporal resolutions capable of capturing coronaries from a single heartbeat, which involve sub-millimeter spatial resolution and a one-third (⅓) (even one-fourth (¼)) of a second complete rotation of the entire x-ray/detector combination.

One shortcoming of CT imaging is its inability to distinguish what has caused the attenuation in the patient (e.g., a small high density, high-Z material, or larger lower density, lower-Z material would be un-differentiable). Imaging pre- and post-injection of contrast, acquisition at different energy (potential on the x-ray tube) or on a different detector altogether have all been described and used to enhance the ability of CT to separate the different materials. For most of those cases, acquiring two scans at different energies would provide enough information to extract the desired material information. However, acquiring two scans is clearly in competition with keeping the best possible temporal resolution.

Furthermore, in addition to preserving the complete temporal resolution, K-edge imaging (where two energy windows are set just below and just above the characteristic energy of the material, for instance 33 keV for Iodine, 80 keV for Gold), requires a wide range of energy for each acquisition, which is not always available.

The ultimate solution for all these situations is somewhat theoretically simple but practically intractable. The solution would be to measure the energy of every events detected. The comparison of the spectral characteristics of the detected beam with the nature of the original x-ray flux would allow for the construction of the presence of the different material inside the object.

The problem in practice is that modern CTs use and require very large fluxes that can easily generate rates well in excess of 100 Million events per sec pre mm$^2$ on the detector. There is no known combination of material and electronic that can support that. Direct conversion detectors (based on heavy semi-conductors like cadmium zinc telluride (CZT) or cadmium telluride (CdTe)) are among the devices with the best chance of getting the necessary information. Still the classical compromise between speed and spectral information will be an extremely difficult task.

First, the charge collection in the semiconductor is determined by the basic properties of the material and the applied bias, which is itself limited by impurities and other factors resulting in a (semi-complete) charge collection time supporting a maximum of few million counts per second, which is nowhere near what is needed. One way to resolve this dilemma is to create many smaller detector channels (or pixels), and, therefore, divide the flux into multiple electronics chains. The problem there is that when the pixels become too small, the charge being collected by one pixel can be "shared" or "seen" by adjacent pixels, altering or even potentially ruining the spectral information that we precisely aim at obtaining. To further complicate things, for both directions (of small or larger pixel) the pulses will overlap creating pile-up. As the pulses overlap more and more, it means that more and more charges are being collected, which means that the charge cloud will progressively mask or decrease the effective bias on the detector, further slowing down the collection, and further exacerbating the pile up problem.

As is described more fully below, aspects of the disclosed technology include an imaging system and method to collect the optimal information and enable the potential of a full spectral CT system. In accordance with an exemplary embodiment, the imaging method includes setting the time frame of the CT acquisition to match or approximately match the acquisition time of PET, which is typically two orders of magnitude slower than current general purpose clinical CT. As the two acquisitions would be simultaneous or substantially simultaneous, and on the same volume of interest, the fact that the CT acquisition is longer (as compared to a standalone CT system acquisition) should not affect negatively the workflow of the PET/CT.

As is described more fully below, the PET/CT system includes 1) a PET system having a timing resolution (TOF performance) that can, for the most part, compensate for an axial gap in the ring geometry (e.g., a gap between adjacent PET detector rings, which is filled or otherwise includes a CT system); and 2) a CT system configured to use the entire (or substantially the entire) PET acquisition time to acquire its own information.

It will be appreciated that with an in-plane PET sensitivity approaching 80% or even 90% in some case, and the injected dose already approaching the limit impose by dosimetry, the 5 to 10 minutes per 100 cm, or 1 to 2 minutes per PET axial field of view (FOV), gives CT almost more than 2 orders of magnitude more time to perform all the necessary acquisition, if the CT acquisition is performed at the same time as the PET acquisition.

Figure 4:
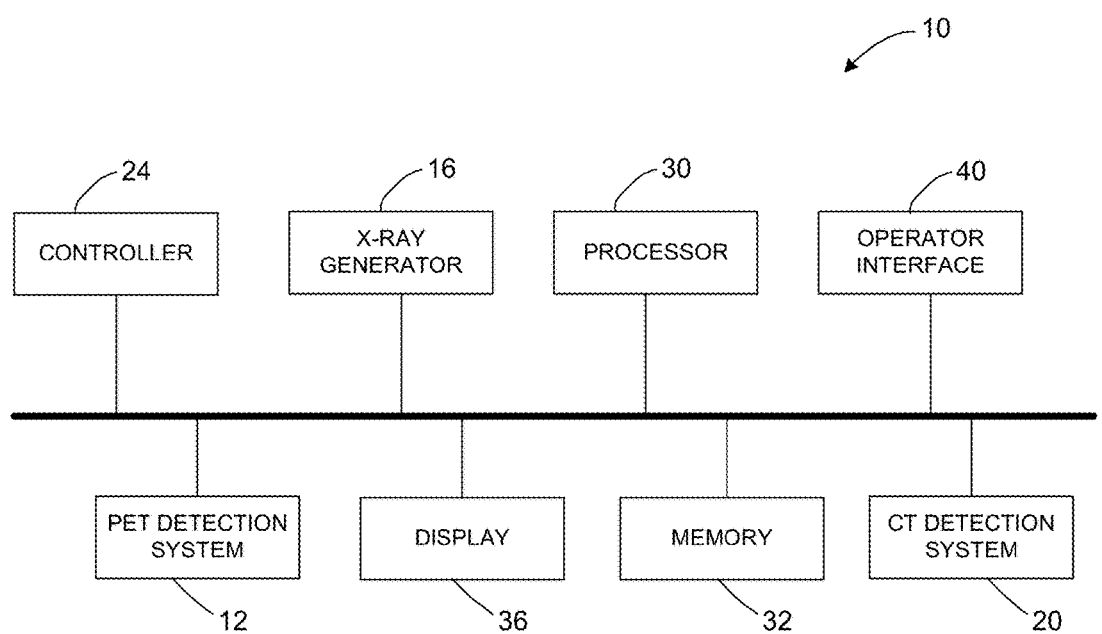
FIG. 4 is a diagrammatic illustration of a PET/CT imaging system in accordance with exemplary aspects of the disclosed technology.

With reference to FIG. 4, a PET/CT system 10 is provided. As is described in more detail below, the PET/CT system 10 includes a PET detection system 12, which includes a detector array or detector arrays positioned circumferentially around a patient positioned on a table or other suitable support. The PET detector array includes an axial gap in which a CT imaging system is provided. The CT imaging system includes an x-ray generator 16 (also referred to as an x-ray source) and a CT detection system 20.

As is described in more detail below, the CT detection system 20 can include a number of components, such as an anti-scatter grid, a detection assembly or series of detectors and a CT digital acquisition system. It will be appreciated that the CT acquisition system can be supported by a rotating gantry. The x-ray generator 16 can be configured to project a beam of x-rays through a suitable filter and/or collimator and toward a detector assembly on the opposite side of the gantry within the axial gap formed in the PET detection system. The plurality of detectors within the CT detection system 20 are configured to sense the projected x-rays that pass through a patient (also referred to as a region of interest or ROI). The digital acquisition system is configured to convert the data representative of x-rays received by the detectors to digital signals for subsequent processing. It will be appreciated that each detector within the CT detection system can be configured to produce an analog electrical signal that represents the intensity of impinging x-ray beam, and hence, the attenuated beam as it passes through the patient.

Rotation of the gantry and operation of the x-ray source are governed by a controller 24. The controller 24 controls the overall functioning and operation of the PET/CT system, including providing power and timing signals to the x-ray source and a gantry motor controller that controls the rotational speed and position of the gantry. A processor (also referred to as an image reconstruction processor) 30 receives samples and digitizes x-ray data from the digital acquisition system and performs high speed reconstruction. The reconstruction image can be stored within memory 32 and shown on display 36.

The system includes an operator interface 40 that can include suitable input devices such as, a keyboard, mouse, voice-activated controller, or any other suitable input apparatus. The display 36 allows the operator to observe the reconstruction image and other data from the processor. The operator interface allows the operator to supply commands and parameters can be used by the processors to provide control signals and information to the data acquisition system, and the controller 24. It will be appreciated that the system can include a table which controls a motorized table to position the patient and gantry.

The following description will discuss various exemplary configurations, which may be employed without departing from the scope of the disclosed technology. This discussion includes various configurations for the PET detection system that would allow simultaneous acquisition of PET data and CT data.

Figure 5:
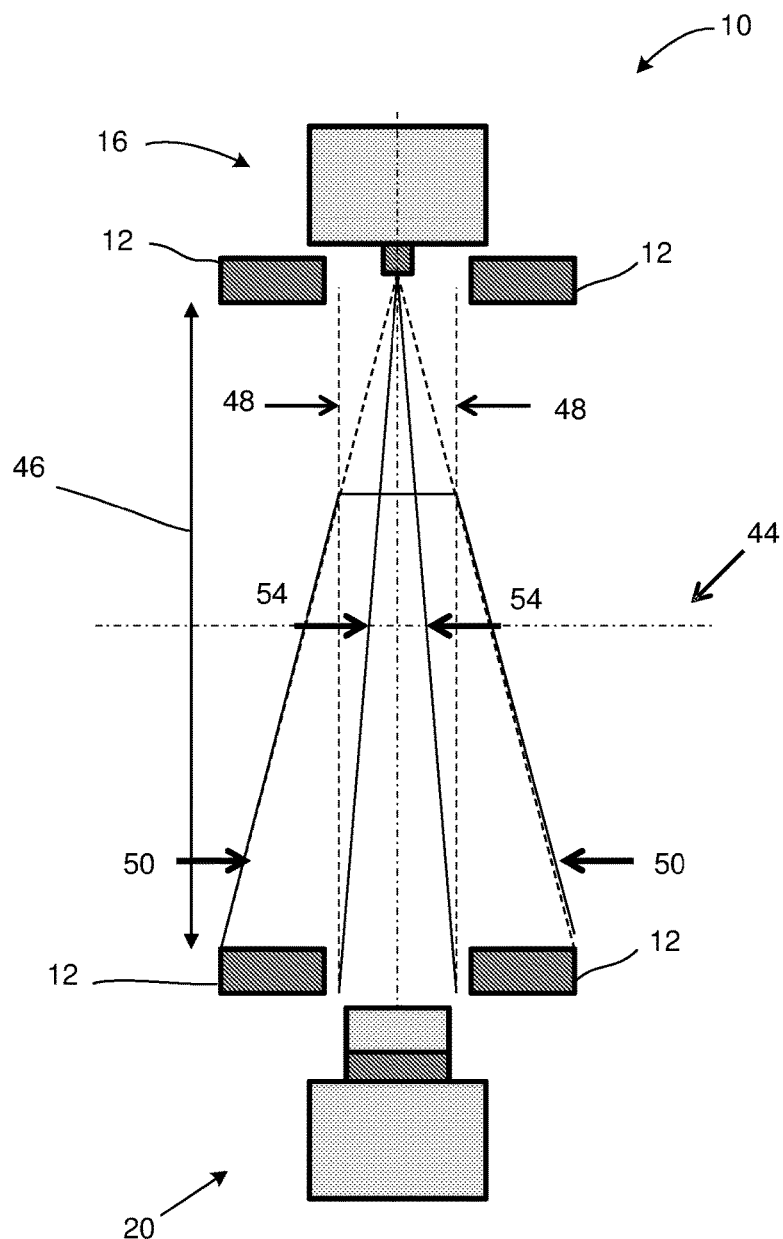
FIG. 5 is a diagrammatic illustration showing an axial sectional view of a PET/CT imaging system in accordance with one exemplary aspect of the disclosed technology.

Referring now to FIG. 5, a first exemplary configuration of a PET/CT system 10 is provided. In FIG. 5, the axial direction is indicated by line 44, and the transaxial FOV is indicated by arrow 46. In this exemplary configuration, the system includes a PET detection system 12 (e.g., including a fixed ring of PET detectors) and a CT assembly or CT system, including an x-ray generator 16 and a CT detection system 20. In the illustrated exemplary configuration, the x-ray generator 16 and the CT detection system 20 are inserted or otherwise positioned and configured to rotate in the gap created by the two fixed sections of the PET detector ring (PET gap is indicated generally by arrows 48; PET axial FOV is indicated generally by arrows 50). In the illustrated embodiment, the CT system has a CT axial FOV indicated generally by arrows 54. In accordance with one exemplary embodiment, the edge of the x-ray beam can be as close as a few tens of millimeters (e.g., less than about 5 centimeters) from the edge of the PET detector gap 48, and typically not farther than this tens of millimeters plus half of the axial span of the CT detector.

In this exemplary configuration, the PET detection system 12 is configured to collect information from detector elements on the same side of the x-ray beam and on the opposite side as well. The proportion of each type is determined by the ratio of the axial extent of the two PET detector rings and the distance of the PET gap 48 (also referred to as axial space or axial gap) between them. PET events can be collected over the entire axial range of the ring (and all possible angles circumferentially). A sensitivity profile can be built, but will fall to zero at the very edge of both axial FOV (AFOV), and should remain flat even over the gap. It will be appreciated that typical, non-gap, cylindrical PET ring exhibits a triangular shape sensitivity profile with its peak exactly in the middle of the axial FOV.

In this configuration, the CT AFOV is, as in any other CT, defined by the intersection on the edge of the cone with the isocenter line. In accordance with one exemplary feature, the size of the PET AFOV will completely include the CT AFOV, and can extend to the very edge of the PET axial extent (with the known caveat that the PET sensitivity will drop to zero at the very edge and the last few slices on either side may be un-usable for lack of counts).

Figure 6:
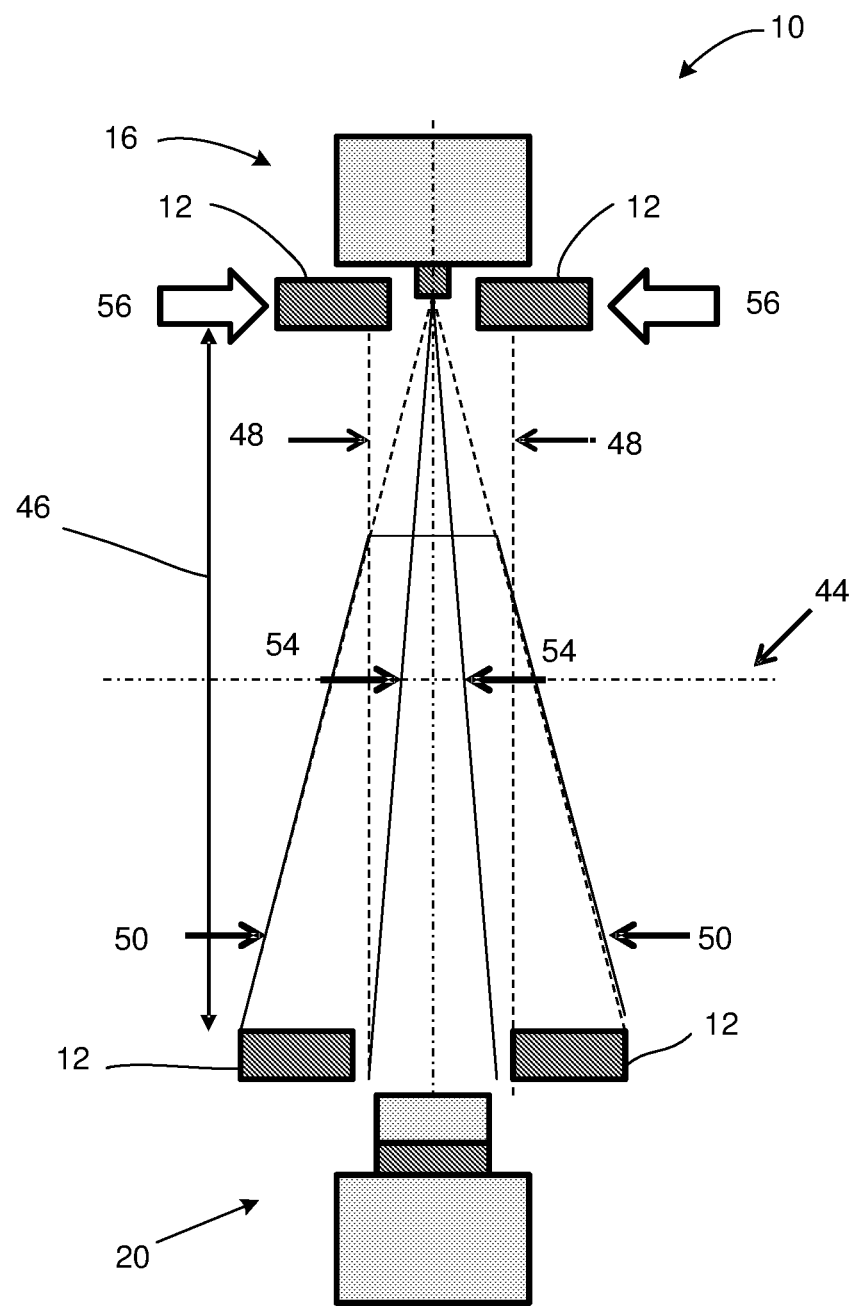
FIG. 6 is a diagrammatic illustration showing an axial sectional view of a PET/CT imaging system in accordance with another exemplary aspect of the disclosed technology.

Referring now to FIG. 6, another exemplary configuration of a PET/CT system 10 is provided. The illustrated exemplary configuration is similar to the previous exemplary configuration, but the gap between the two sections of the PET ring is variable (variable PET gap is indicated generally by arrows 56). It will be appreciated that the PET gap can be configured to follow as tightly as possible the cone geometry of the x-ray beam generated by the x-ray generator 16. As in the previous exemplary configuration, the distance between the edge of the x-ray beam and the edge of the active PET detector will be substantially constant (e.g., between about 5 millimeters and about 50 millimeters). It will be appreciated that one feature of this arrangement is that the PET rings will rotate with the CT assembly to preserve the relative geometry between the two systems. It will be appreciated that forming LORs from a rotating PET ring can be accomplished if proper angular positioning is given to the system (noting that motion will be in the millisecond range, while coincidences are built with picoseconds accuracy).

In this exemplary configuration, the CT imaging parameter and FOV can be the same as described above in connection with the previous exemplary configuration. It will be appreciated that the PET data, however, will differ slightly. A larger portion of the counts will come from slices in the object included in the PET gap as the geometry becomes more favorable. It will be further appreciated that the extra counts in the PET gap will come from the edge of the AFOV, which can now extend to the mid-point between the two AFOV (virtual line joining the end of the AFOV and the isocenter line).

It will be appreciated that since the PET rings are rotating (e.g., in sync with the CT system), the composition of the PET detection system 12 excludes the use of standard photomultiplier tubes, as the variable position of the tubes with respect to the earth magnetic field would cause noticeable gain variation. It will be appreciated that magnetic insulation would be possible, or, as recently described, the system can make use of solid-state SiPM sensors, on which even strong magnetic fields have negligible effect. In addition, the use of SiPM should also allow for better timing or time-of-flight imaging performance, in turn providing a better positioning of events inside the PET gap.

Figure 7:
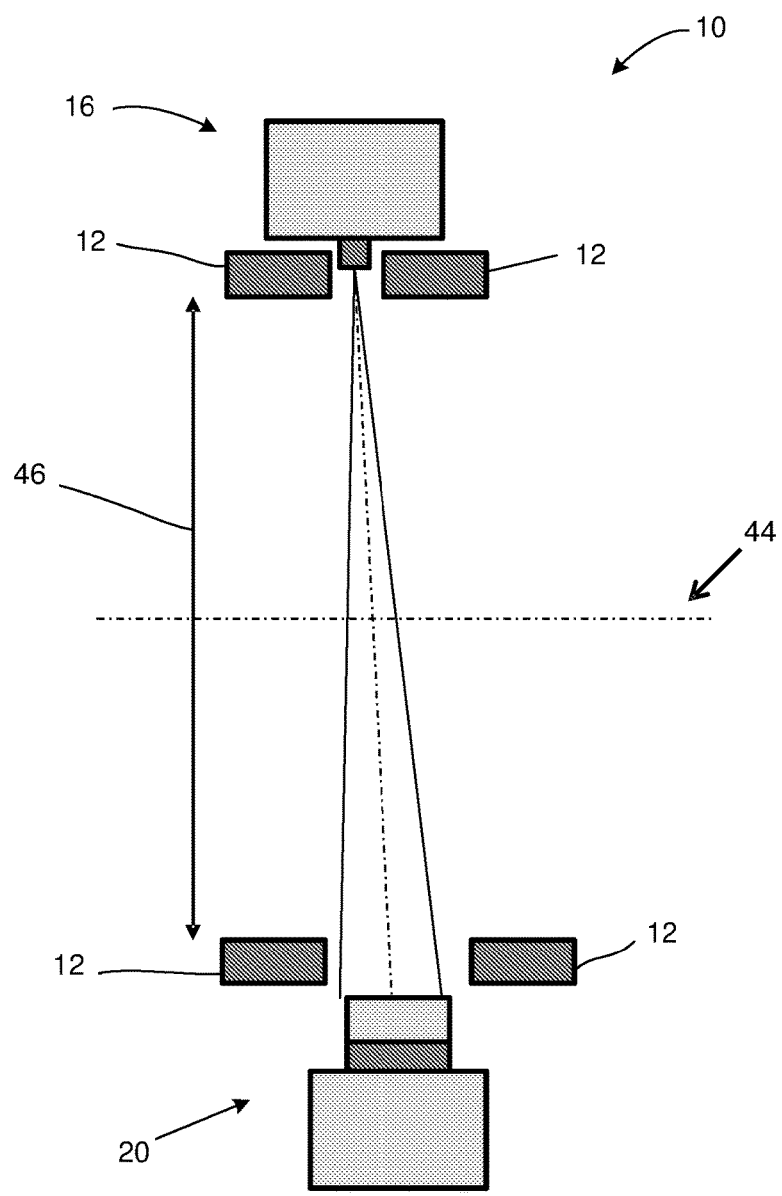
FIG. 7 is a diagrammatic illustration showing an axial sectional view of a PET/CT imaging system in accordance with another exemplary aspect of the disclosed technology.

Referring now to FIG. 7, another exemplary configuration of a PET/CT system 10 is provided. It will be appreciated that the exemplary configuration illustrated in FIG. 7 represents a slight modification to the exemplary configuration described above with respect to FIG. 6. In the current exemplary configuration, the x-ray generator 16 is positioned in an oblique angle, so that one edge of the beam forms a flat surface (as opposed to a cone on the other side). It will be appreciated that this may be advantageous for long axial studies. The rest of the imaging characteristics of the prior exemplary configuration should be the same for this exemplary configuration.

Figure 8:
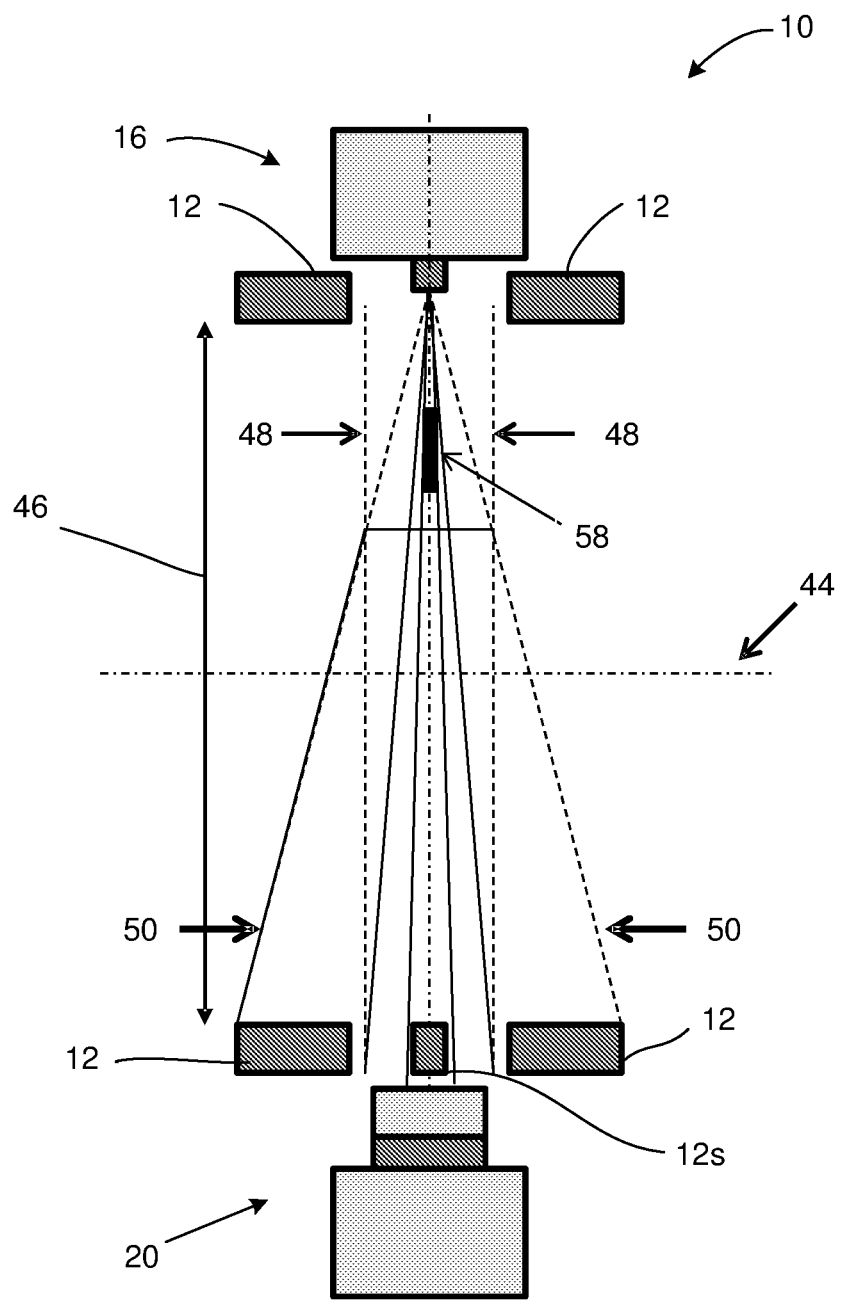
FIG. 8 is a diagrammatic illustration showing an axial sectional view of a PET/CT imaging system in accordance with another exemplary aspect of the disclosed technology.

Referring now to FIG. 8, another exemplary configuration of a PET/CT system 10 is provided. The exemplary configuration includes an additional feature that can be inserted into one or more of the above-described exemplary configurations (e.g., "standard" and "tight" geometry, and technically also possible for the "oblique" geometry). As shown in FIG. 8, the PET/CT system includes a beam blocker 58, which is positioned and configured to create a gap in the cone direction allowing for a PET detector unit 12s to be positioned in the "shadow" of the beam blocker 58. It will be appreciated that this can be useful in the case of very large CT coverage, where the combination of the large gap and the finite TOF performance of the PET detector may decrease the quality of the reconstructed PET information.

In this exemplary configuration, the CT will image two sets of slices, separated by a gap. Axial movement (e.g., via CT helical protocols) can be employed to recover the entire image set.

It will be appreciated that PET would be very similar to the "base" configurations with extra counts due to the presence of the PET detector 12s inserted in the x-ray beam shadow. In this exemplary configuration, the AFOV for PET would remain the same as the corresponding base configuration without the beam blocker and the additional PET detector.

Figure 9:
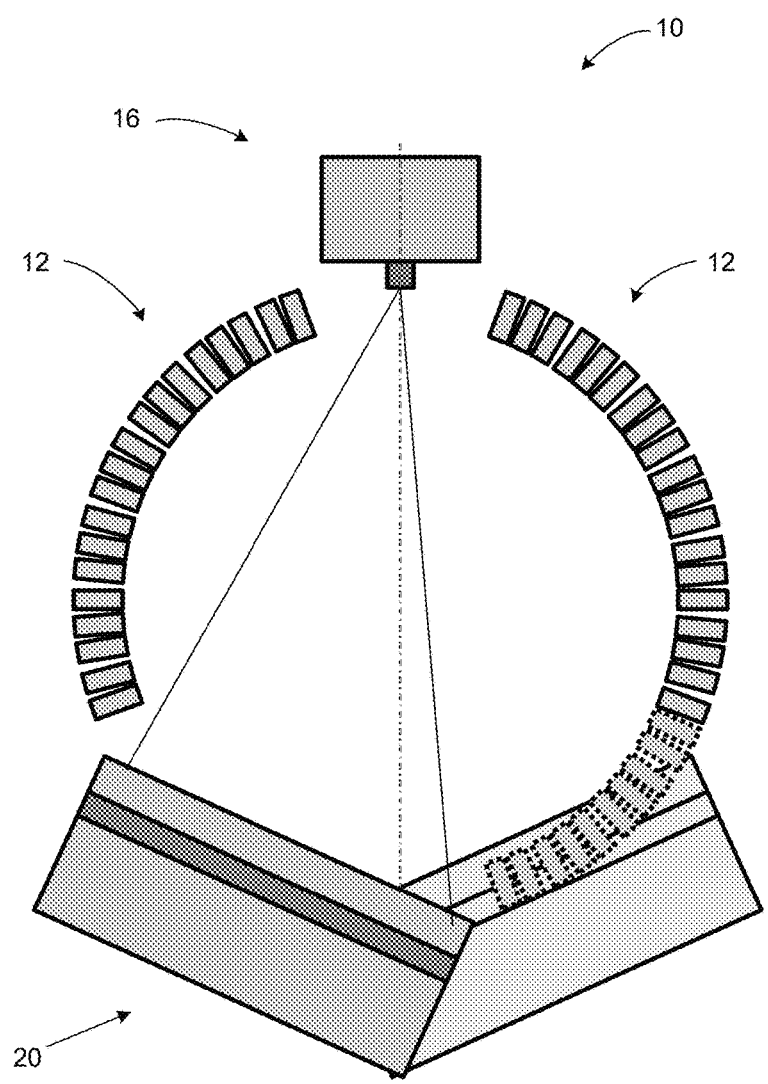
FIG. 9 is a diagrammatic illustration showing a transaxial view of a PET/CT imaging system in accordance an exemplary aspect of the disclosed technology.

The above-described exemplary configurations were illustrated in connection with an axial section of the imaging system. For purposes of further explanation, FIG. 9 is a diagrammatic illustration of a transaxial view of an exemplary PET/CT configuration in accordance with aspects of the disclosed technology.

First, it is noted that the fan angle of a typical scanner is around +/−50 degrees, leaving large angular gaps between the edge of the CT detector and the X-ray beam. In these gaps, there is no reason not to have a PET detector arrangement. Applying this to the "standard" configuration would, however, force the PET assembly to rotate in sync with the CT as in the other exemplary configurations described above.

Second, some CT systems currently in use are also built in a transaxially asymmetric configuration. This geometry is entirely compatible with the CT reconstruction principles, but requires an entire 360 degree rotation (as opposed to a minimum of 180+ fan angle in the typical case).

By rotating with the CT assembly, the detector components positioned in the transaxial angular gap on the CT would all contribute to gathering PET information in the CT volume as the CT volume is being imaged.

Another choice for the system, with partial imaging benefit compared to the exemplary configurations described above, but offering a simpler construction, would be to put the CT immediately after the PET FOV either in a leading or in a trailing position (in the Z direction). Since most of the acquisitions are much longer than the size of either AFOV, (e.g., 100 cm acquisition for a 6 cm CT AFOV and 15-20 cm PET AFOV) the workflow would be very marginally affected.

While the above-described exemplary configurations include an x-ray generator relatively close to a PET detection system, it will be appreciated that one advantage of these exemplary configurations is that the flux itself is about 10 to about 100 times lower intensity compared to conventional CT scanner. In addition, the scatter radiation would be at much lower energy. It would still "occupy" some of the PET detection bandwidth, but can be rejected very early in the process.

Referring now to FIGS. 10-13, another exemplary configuration of a PET/CT system is provided. As is described more fully below, the PET/CT system is configured to include a radiation shield configured to rotate in synchronization with the x-ray generator and the CT detection system.

In one or more of the above-described exemplary configurations, it will be appreciated that the proximity in the axial direction of the at least two PET detector rings and the x-ray beam can cause spillover onto the PET detection system. While there should be no direct overlap between the nominal beam geometry and the PET detector, a few factors will be discussed in connection with the exemplary configuration described below.

Figure 10:
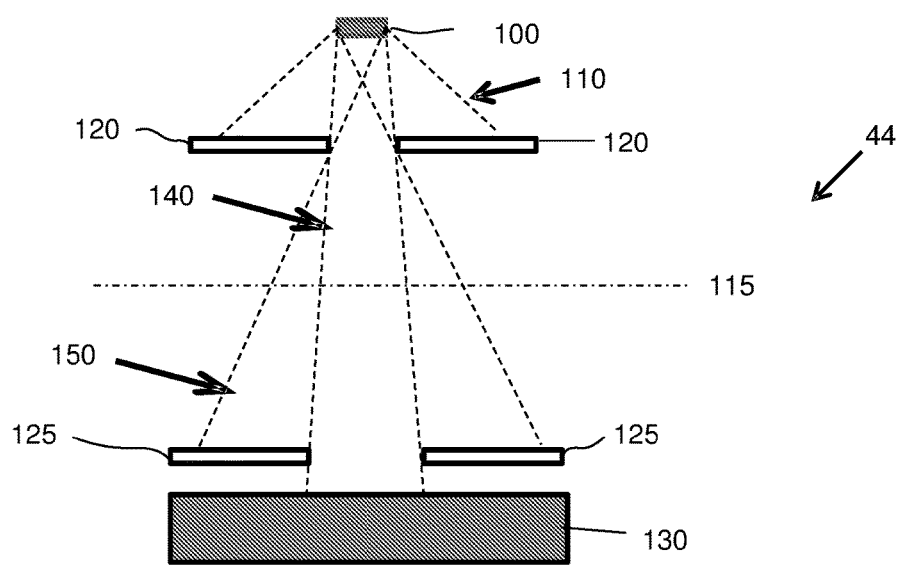
FIG. 10 is a diagrammatic illustration showing principles related to the formation of a penumbra area.

First, there is the penumbra effect. Due to the finite size of the x-ray focal point of the x-ray generator, the definition of the beam geometry will not be exact and will inevitably include a penumbra area. FIG. 10 schematically illustrates a penumbra effect. FIG. 10 shows an x-ray source 100 having x-ray flux 110. The z-axis is designated by reference numeral 115. A pre-patient collimator 120 and a post-patient collimator 125 are positioned between the x-ray source 100 and a detector 130. An umbra area is designated at 140 and a penumbra area is designated as 150.

Figure 11:
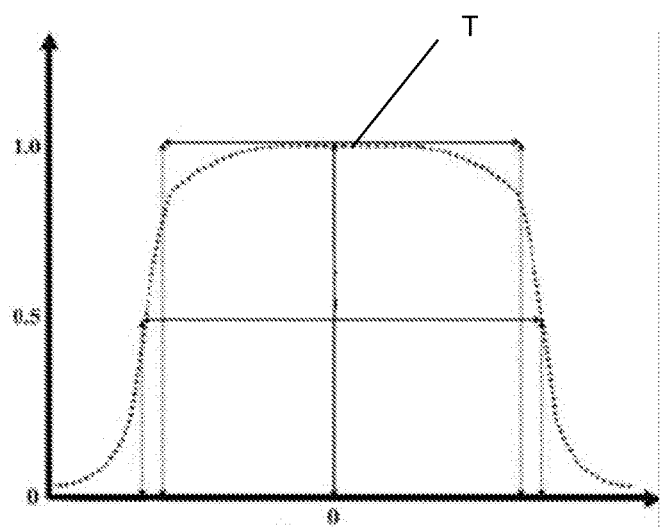
FIG. 11 is a diagrammatic illustration showing exemplary x-ray beam width.

FIG. 11 illustrates an example of a potential beam profile along the Z-axis, where the beam profile may drop from the nominal; width "T", which can be very fast.

Figure 12:
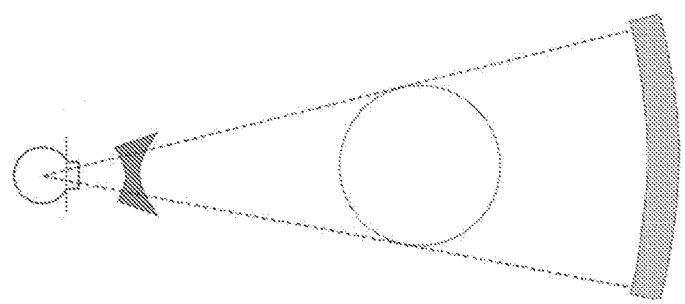
FIG. 12 is a diagrammatic illustration of an exemplary x-ray beam, which may be employed in connection with aspects of the disclosed technology.

Referring to FIG. 12, in the transaxial plane, the x-ray beam can be formed by a so-called bow-tie filter, which is configured to leave the beam with the highest intensity in the iso-center and rapidly attenuate the beam as its progresses along the fan angle direction. The overall goal of this approach is to get a more uniform x-ray flux on the CT detector after it has traversed the patient, approximated by a cylinder for the purpose of the discussion. It will be appreciated from this figure that the part of the x-ray beam going through to middle of the filter (where it is the thinnest) will have less attenuation but will be the most attenuated when traversing the object (patient). The x-ray beam will progressively decrease in intensity as larger angles are considered but, will have progressively less and less of the object to traverse.

The second class of effect potentially causing the beam to extend beyond its nominal geometry is due to the very interaction of the x-ray beam with matter (the patient). A large fraction of the x-ray photons will either traverse the object unaffected or be completely absorbed (via the photoelectric effect). A significant fraction of the x-ray photons will only be scattered via the Compton and Thompson effect, causing the beam to be diverted from its original path and lose energy (in relation to the angle at which the photon has been diverted). Scattered photons will undergo the same process: either continuing on, being absorbed or being scattered again. Bottom line, a significant portion of the beam will eventually get out of the object in a completely different trajectory and reach either the CT or the PET detector.

It will be appreciated that the overall behavior of the beam passing through an abject and its associated contamination (with respect to the original beam) is complex and depends on many factors, including the spectral composition of the beam before entering the object, the size, density, composition of the object, the exact geometry between the source and the object, and the exact design of the detection system.

The present discussion is concerned only with the scattered radiation exiting the original beam path and possibly entering the PET detector area (it is possible for photons to be scattered and remain in the original path of the CT detector). Aspects of the disclosed technology discussed below address the situation where more attenuation of the scattered radiation is required (e.g., to further decrease the PET electronics bandwidth or to operate the CT at higher than required current intensity).

Figure 13:
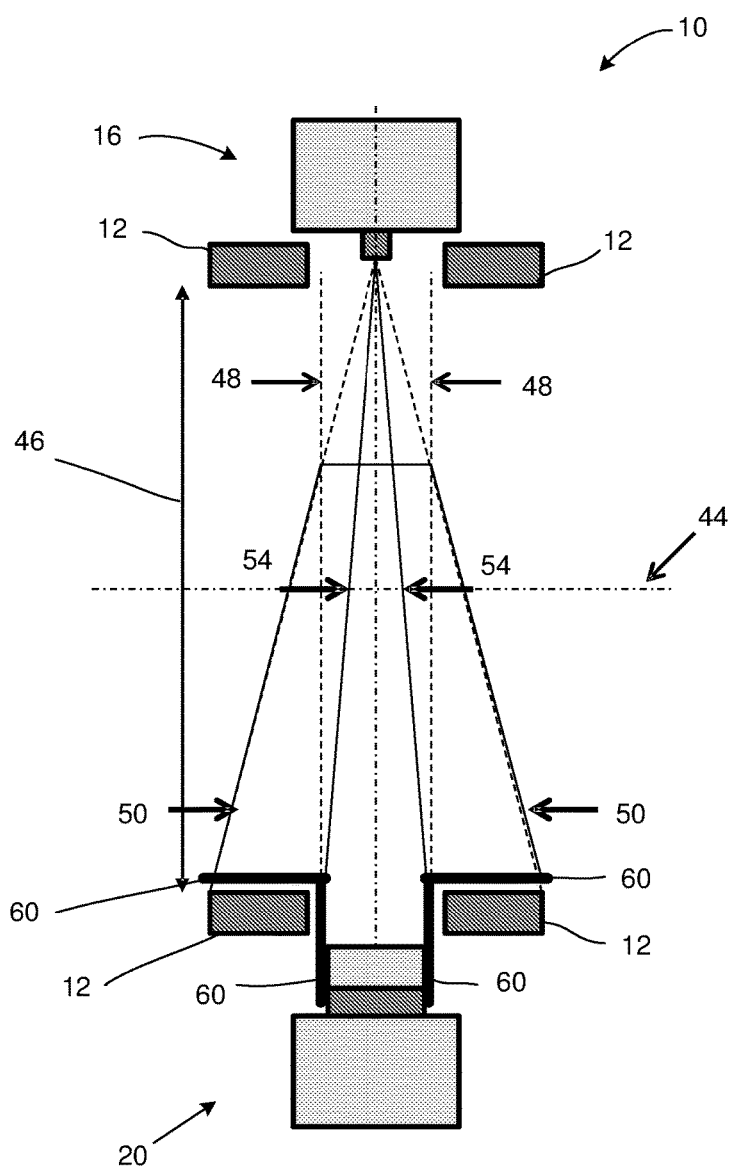
FIG. 13 is a diagrammatic illustration showing an axial sectional view of a PET/CT imaging system in accordance with another exemplary aspect of the disclosed technology.

Referring now to FIG. 13, another exemplary configuration of a PET/CT system 10 is provided. It will be appreciated that the system illustrated in FIG. 13 is similar to the system illustrated in FIG. 5 (like reference numerals indicate like elements in the two figures). The exemplary configuration of FIG. 13 includes a radiation shield 60 disposed over or covering a portion of the PET detection system. The radiation shield can be coupled or connected to the CT detection system, such that it can rotate in conjunction or in synchronization with the CT detection system to ensure that a minimum amount of scattered radiation would affect the PET detection system (in the axial plane). Alternatively, the radiation shield can be releasably coupled to the CT detection system. In accordance with one aspect, the radiation shield would be disposed over or only partially cover the PET detection system circumferentially, and leave most of the PET detector ring unaffected to operate with the maximum sensitivity to the PET-specific radiation.

In accordance with one aspect, the radiation shield would be disposed over or cover the entire axial extent of the PET detection system. Alternatively, the radiation shield would be disposed over or cover only a portion of the axial extent of the PET detection system (possibly depending on the amount of desired reduction of the scattered radiation). Transaxially, the radiation shield would be disposed over or cover an arc roughly corresponding to the CT detector size, but could also be shorter or longer depending on the desired effect and given the particular design of the bow-tie filter.

It will be appreciated that the above-described exemplary PET/CT configurations allow for a variety of imaging options and applications without departing from the scope of the disclosed technology. It will be further appreciated that the above-described exemplary configurations of the PET/CT system can extend the imaging time for CT from roughly one second to around 100 seconds, in accordance with one exemplary embodiment. Of course, it will be appreciated that the longer acquisition time for CT does not increase the radiation dose to the patient. So it means that the x-ray tube and associated power and controls would be modified to allow this new setup to be implemented.

With the increase acquisition time, the normal multiple rotation/acquisition mode to acquire multiple energy information is possible. Two or more rotations at different kVp could be the easiest and most direct way of acquiring the necessary information.

It will be appreciated that having more time for performing the CT acquisition can solves or at least improve upon a problem for photon counting system—the count rate. With a reduction of the rate by a factor up to 100, it then puts a CZT or CdTe-based system in an optimal or near-optimal range for capturing the entire information from a charge collection point of view.

It is also to be considered that this rate reduction may enable a scintillator-based system. Currently, fast and high volume crystal like lutetium-based crystals (LSO, LYSO, LFS and the like) and new solid-state light sensor like SiPM could be fast enough to get to the 1 Mcps/mm$^2$ level. It will be appreciated that direct conversion would continue to have a systematic advantage from the number of quanta generated per given x-ray energy deposited, but scintillator-based may have other engineering (e.g., cooling and/or uniformity) or cost advantage.

It will be appreciated that these new exemplary imaging configurations will bring new ways of acquiring the data, as well as new ways to interpret the information.

It will be appreciated that the PET information obtained from the above-described gapped arrangement should be substantially the same as the arrangement without the gap with a decreased sensitivity (roughly proportional to the square of the loss of solid angle). This is assuming that the gap is not too large and that the PET system has an adequate TOF resolution.

It will be appreciated that the imaging methodology and system setup can be configured such that the overlap region between PET and CT is located at the best area for PET, which has a maximum sensitivity in the middle of the AFOV (provided that the gap dimension is less than half of the dimension of each PET ring), and the additional lateral information (from coincidences from detector elements on the same side of the CT unit) is desirable for adequate correction, scatter correction in particular.

It will be appreciated that while the CT sub-system and associated acquisition protocols are designed to use substantially all the acquisition time required by PET, the CT sub-system remains capable of faster (complete) acquisition (defined as complete rotation of the unit about the patient). It is therefore possible, while keeping the same total x-ray dose to the patient, to perform multiple rotations of the CT-sub-system. The multiple rotations can span and acquire data in multiple dimensions described below.

Time—By repeating the same imaging of a period of time, an assessment of the patient/organ motion could be done.

Energy—By performing the same imaging using different energy settings, assessment of the material properties of the patient could be inferred.

Sampling—By adjusting the x-ray beam (e.g., focal spot) and/or the detector position between rotation, a better sampling (and in turn spatial resolution) could be realized.

In accordance with one exemplary application of the above-described PET/CT system, it will be appreciated that all the information collected during all rotations, can also be combined into the final global image. The multiple rotations of the CT system can be acquired in the so-called circular mode (where there is no axial translation of the patient and all rotations are covering the same region); or in a helical mode, where a slow axial translation will still produce sufficient overlap between rotation to produce multiple estimate over time.

It will be appreciated that the current configuration offers a way to obtain an optimal spectral system with only a compromise in time in a study that is anyway forced into a much longer timeframe: PET.

K-edge imaging is a special case of spectral imaging. While simpler 2-material separation have reasonably accurate surrogates (e.g., dual-tube or kV switching systems), true K-edge imaging of sometime minute quantities of material (e.g., gold nano-particles) would benefit significantly from a more optimal system, such as is described above in connection with the illustrated exemplary configurations. In fact, a full spectral CT and a state-of-the-art TOF PET system could provide exquisite molecular imaging capability.

Radiomics is the science of extracting quantitative features from a region of interest in a CT (texture, shape, asymmetry, density, etc.), PET or MR image set, with the goal being to correlate this information with other elements of the patient genotype or phenotype. It will be appreciated that the above-described exemplary configurations and features would ensure that the best possible data is available for the analysis, PET and full spectral CT characterization of a tumor, joint pharmacokinetic analyses, Although the disclosed technology has been shown and described with respect to a certain preferred aspect, embodiment or embodiments, it is obvious that equivalent alterations and modifications will occur to others skilled in the art upon the reading and understanding of this specification and the annexed drawings. In particular regard to the various functions performed by the above described elements (components, assemblies, devices, members, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary aspect, embodiment or embodiments of the disclosed technology. In addition, while a particular feature of the disclosed technology may have been described above with respect to only one or more of several illustrated aspects or embodiments, such feature may be combined with one or more other features of the other embodiments, as may be desired and advantageous for any given or particular application.

What is claimed is:

1. A PET/CT imaging system comprising:
   a PET detection system comprising a plurality of detector rings, wherein at least two adjacent detector rings within the plurality of detector rings are positioned with an axial space between the at least two adjacent detector rings;
   a CT system comprising an x-ray generator and a CT detection system, wherein the x-ray generator is positioned and configured to generate an x-ray beam within the axial space between the at least two adjacent detector rings for detection by the CT detection system;
   a processor operatively coupled to the PET detection system and the CT detection system, wherein in response to simultaneously acquired radiation by the PET detection system and the CT detection system, the processor is configured to process signals received from the PET detection system and the CT detection system independently and/or jointly; and
   a controller operatively coupled to the CT system, wherein the controller is configured to reduce a flux of the x-ray generator as compared to a flux of an x-ray generator in a standard CT system such that a PET acquisition time and a CT acquisition time are substantially equal.

2. The PET/CT imaging system of claim 1, wherein at least one detector ring of the at least two adjacent detector rings has an axial dimension, and wherein the PET/CT imaging system is configured such that an edge of the x-ray beam generated by the x-ray generator is spaced no more than 5 centimeters from an edge of the at least one ring on the PET detection arrangement along the axial dimension.

3. The PET/CT imaging system of claim 1, wherein the x-ray generator is positioned and configured to generate an x-ray beam between the at least two adjacent detector rings such that the x-ray beam generated by the x-ray generator is spaced no more than 5 centimeters from edges of the at least two adjacent detector rings.

4. The PET/CT imaging system of claim 1, wherein the PET detection arrangement is configured to include time-of-flight (TOF) capability.

5. The PET/CT imaging system of claim 1, wherein the CT system is configured to include energy discriminating, photon counting capability.

6. The PET/CT imaging system of claim 1, wherein the plurality of detector rings of the PET detection system are stationary and the x-ray generator and CT detection system are configured to rotate.

7. The PET/CT imaging system of claim 1, wherein the plurality of detector rings of the PET detection system are configured to rotate together with the x-ray generator and the CT detection system.

8. The PET/CT imaging system of claim 7, wherein at least two adjacent detectors on a first portion of the at least two adjacent detector rings are spaced apart by a first axial distance and two adjacent detectors on a second portion of the at least two adjacent detector rings are spaced apart by a second axial distance that is greater than the first axial distance.

9. The PET/CT imaging system of claim 8, wherein at least one of the detector rings is comprised of one or more partial detector rings.

10. The PET/CT imaging system of claim 8, wherein the first axial distance and the second axial distance are configured to correspond to axial dimensions of the x-ray beam generated by the x-ray generator.

11. The PET/CT imaging system of claim 7, wherein the axial space between the at least two adjacent detector rings is variable.

12. A PET/CT imaging system comprising:
a PET detection system comprising a plurality of detector rings, wherein at least two adjacent detector rings within the plurality of detector rings are positioned with an axial space between the at least two adjacent detector rings;
a CT system comprising an x-ray generator and a CT detection system, wherein the x-ray generator is positioned and configured to generate an x-ray beam within the axial space between the at least two adjacent detector rings for detection by the CT detection system;
a processor operatively coupled to the PET detection system and the CT detection system, wherein in response to simultaneously acquired radiation by the PET detection system and the CT detection system, the processor is configured to process signals received from the PET detection system and the CT detection system independently and/or jointly;
a radiation shield disposed at least partially over a circumference of the detector rings of the PET detection system, wherein the radiation shield is configured to rotate in synchronization with the x-ray generator and the CT detection system; and
a controller operatively coupled to the CT system, wherein the controller is configured to reduce a flux of the x-ray generator as compared to a flux of an x-ray generator in a standard CT system such that a PET acquisition time and a CT acquisition time are substantially equal.

13. The PET/CT imaging system of claim 12, wherein the radiation shield is disposed over the entire axial extent of the detector rings of the PET detection system.

14. The PET/CT imaging system of claim 12, wherein the radiation shield is disposed over a portion of the axial extent of the detector rings of the PET detection system.

15. The PET/CT imaging system of claim 12, wherein the radiation shield is comprised of a single homogeneous material or one or more layers of material.

16. An imaging method for imaging a given region of interest (ROI), the imaging method being carried out using a PET/CT imaging system, the PET/CT imaging system including a PET detection system comprising a plurality of detector rings, wherein at least two adjacent detector rings within the plurality of detector rings are positioned with an axial space between the at least two adjacent detector rings; and a CT system comprising an x-ray generator and a CT detection system, wherein the x-ray generator is positioned and configured to generate an x-ray beam in the axial space between the at least two adjacent detector rings for detection by the CT detection system, the imaging method comprising: simultaneously collecting PET imaging data using the PET detection system and CT imaging data using the CT detection system for a given imaging time;
wherein the PET detection system has a standard PET imaging time for the given ROI and the CT system has a standard CT imaging time for the given ROI that is less than $\frac{1}{10}$ the standard PET imaging time, and wherein an imaging time for the collecting of CT imaging data and an imaging time for the collecting of PET imaging data are both set to be substantially equal to the standard PET imaging time.

17. The imaging method of claim 16, wherein the imaging time for the simultaneous collecting of PET imaging data and CT imaging data is set to be more than 10 times the standard CT imaging time.

18. The imaging method of claim 16, wherein the imaging time for the simultaneous collecting of PET imaging data and CT imaging data is set to be between 10 times the standard CT imaging time and 100 times the standard CT imaging time.

19. The imaging method of claim 16, further comprising processing signals representative of the simultaneously collected PET imaging data and CT imaging data independently and/or jointly.

20. The imaging method of claim 16, wherein the imaging time for collecting the CT imaging data is set to be no less than 10 seconds.

21. The imaging method of claim 16, wherein the imaging time for collecting the CT imaging data is set to be between 10 seconds and 100 seconds.

22. The imaging method of claim 16, wherein the CT imaging data is collected in an axial step-and-shoot mode or in a helical scan mode.

* * * * *